United States Patent
Ekvall et al.

(10) Patent No.: US 10,406,033 B2
(45) Date of Patent: Sep. 10, 2019

(54) SYSTEMS AND METHODS FOR NON-INVASIVE MEASUREMENT OF CASSETTE PRESSURE

(71) Applicant: NOVARTIS AG, Basel (CH)

(72) Inventors: Johan Ekvall, Laguna Beach, CA (US); Paul J. Essex, Rancho Santa Margarita, CA (US); Kirk Todd, Yorba Linda, CA (US)

(73) Assignee: Novartis AG, Basel (CH)

( * ) Notice: Subject to any disclaimer, the term of this patent is extended or adjusted under 35 U.S.C. 154(b) by 98 days.

(21) Appl. No.: 15/691,885

(22) Filed: Aug. 31, 2017

(65) Prior Publication Data

US 2018/0055688 A1  Mar. 1, 2018

Related U.S. Application Data

(60) Provisional application No. 62/382,351, filed on Sep. 1, 2016.

(51) Int. Cl.
*A61F 9/007* (2006.01)
*A61M 1/00* (2006.01)
(Continued)

(52) U.S. Cl.
CPC .............. *A61F 9/008* (2013.01); *A61B 34/25* (2016.02); *A61M 1/0025* (2014.02); *G01L 9/0077* (2013.01); *A61B 2562/0247* (2013.01); *A61F 2009/00844* (2013.01); *A61M 2205/12* (2013.01); *A61M 2205/3306* (2013.01);
(Continued)

(58) Field of Classification Search
CPC . A61B 34/25; A61B 2562/0247; A61F 9/007; A61F 9/008; A61F 2009/00844; A61M 1/00; A61M 1/0025; A61M 2205/12; A61M 2205/3306; A61M 2205/3331;
(Continued)

(56) References Cited

U.S. PATENT DOCUMENTS

| 3,590,640 A | * | 7/1971 | Cindrich | G01B 9/021 |
| | | | | 250/231.19 |
| 5,148,807 A | * | 9/1992 | Hsu | A61B 3/165 |
| | | | | 600/400 |

(Continued)

FOREIGN PATENT DOCUMENTS

| GB | 1419111 A | * 12/1975 | .......... G01L 9/0077 |
| WO | 88/04126 A1 | 6/1988 | |
| WO | 2004/061399 A2 | 7/2004 | |

*Primary Examiner* — Nguyen Q. Ha

(57) ABSTRACT

A method and system provide a surgical system including a cassette, a console and an interferometric pressure sensing system coupled with the console. The cassette is for exchanging material with a patient and includes a wall and a reflector. The wall undergoes a deflection in response to a nonambient internal cassette pressure. The console is coupled with the cassette. The interferometric pressure sensing system is coupled with the console. The interferometric pressure sensing system includes a light source and a detector. The light source provides a first portion of light that is reflected off of the reflector and a second portion of light that bypasses the reflector. The first portion and the second portion of light are recombined to form an interference pattern. The deflection corresponds to a shift in the interference pattern detectable by the detector.

19 Claims, 4 Drawing Sheets

(51) Int. Cl.
  *G01L 11/02* (2006.01)
  *A61F 9/008* (2006.01)
  *G01L 9/00* (2006.01)
  *A61B 34/00* (2016.01)
(52) U.S. Cl.
  CPC ............... *A61M 2205/3331* (2013.01); *A61M 2210/0612* (2013.01)
(58) Field of Classification Search
  CPC ......... A61M 2210/0612; G01L 9/0077; G01L 11/02
  See application file for complete search history.

(56) References Cited

U.S. PATENT DOCUMENTS

| | | | |
|---|---|---|---|
| 5,628,731 A * | 5/1997 | Dodge | A61M 1/0058 128/DIG. 12 |
| 5,830,176 A | 11/1998 | MacKool | |
| 6,955,073 B2 | 10/2005 | Morgan et al. | |
| 7,272,976 B2 | 9/2007 | Gajdeczko et al. | |
| 7,845,235 B2 | 12/2010 | Sandu et al. | |
| 8,011,905 B2 | 9/2011 | Artsyukhovich et al. | |
| 8,398,582 B2 | 3/2013 | Gordon et al. | |
| 9,119,701 B2 | 9/2015 | Gordon | |
| 2002/0173711 A1* | 11/2002 | Walton | A61B 3/165 600/398 |
| 2007/0146661 A1* | 6/2007 | Eussen | G03F 7/70516 355/30 |
| 2009/0262358 A1* | 10/2009 | Russell | A61M 16/08 356/450 |
| 2011/0137240 A1* | 6/2011 | Wiegel | A61M 5/142 604/67 |
| 2016/0195445 A1* | 7/2016 | Olivier | G01L 7/06 73/384 |
| 2017/0202513 A1* | 7/2017 | Schmidt | A61B 5/00 |

* cited by examiner

SYSTEMS AND METHODS FOR NON-INVASIVE MEASUREMENT OF CASSETTE PRESSURE

FIELD

The present disclosure relates to ophthalmic surgical systems and methods. More particularly, the present disclosure relates to techniques for measuring cassette pressure in a surgical system.

BACKGROUND

Ophthalmic surgery frequently involves the removal of fluid and/or tissue from the eye and replacement of the material removed with a fluid such as a balanced salt solution (BSS). In order to remove material, a cannula connected to an aspiration line is inserted into an incision in the eye. The aspiration line is coupled to a console that includes electronics, a control system, a vacuum source such as a peristaltic pump and a fluid source. The vacuum source provides a vacuum to the aspiration line. The vacuum in the aspiration line causes material to flow from the eye and through the aspiration line. To maintain intraocular pressure, another cannula connected to an irrigation or infusion line is inserted into another incision in the eye. The irrigation line is connected to a fluid source in the console. The fluid source may be a reservoir of BSS that can be pressurized to greater than the ambient pressure. When the fluid source is pressurized, the fluid flows is forced out of the fluid source, through the irrigation line and into the eye.

During such surgery, it is desirable to isolate biological material removed from the eye from the vacuum pump. To do so, cassettes are used. A cassette typically fits within a receptacle within the console. Tubing from the aspiration line is connected to a port in the cassette. The cassette is connected to the vacuum source via another port. The vacuum source applies a vacuum to the cassette, which provides the vacuum to the aspiration line. The suction in the aspiration line causes biological material to flow from the eye into the cassette, where the biological material is stored. Thus, the biological material is isolated from the vacuum pump. To provide fluid to the eye, another cassette coupled to a pressure or fluid source and to the irrigation line may be used in an analogous manner.

A pressure sensor may be used to monitor pressure within the cassette during use. For example, a rubber membrane may flex in response to the internal pressure of the cassette. This deflection may cause the membrane to touch a contact sensor. Thus, the pressure may be determined. Alternatively, a sensor may provide light that is reflected off of the membrane at an oblique angle. The reflected light is provided to a sensor. Changes in the position of the light correspond to changes in the internal pressure.

There may be drawbacks to such mechanisms for measuring internal pressure of the cassette function. For example, use of reflected light may not provide sufficiently sensitivity to the internal pressure. Further, the flexible membrane adds to the cost of each of the cassettes, which are disposable. Internal pressure sensors may be subject to the biological material removed from the eye. Thus, such sensors may fail. These sensors also add to the cost of the disposable cassettes.

Accordingly, what is needed is an improved mechanism for monitoring the internal pressure of a cassette in a surgical system.

SUMMARY

A method and system provide a surgical system including a cassette, a console and an interferometric pressure sensing system coupled with the console. The cassette is for exchanging material with a patient and includes a wall and a reflector. The wall undergoes a deflection in response to a nonambient internal cassette pressure. The console is coupled with the cassette. The interferometric pressure sensing system is coupled with the console. The interferometric pressure sensing system includes a light source and a detector. The light source provides a first portion of light that is reflected off of the reflector and a second portion of light that bypasses the reflector. The first portion and the second portion of light are recombined to form an interference pattern. The deflection corresponds to a shift in the interference pattern detectable by the detector.

According to embodiments of the method and system disclosed herein, the internal pressure of the cassette may be more accurately measured, may not require the use of sensors internal to the cassette and may not require expensive additions to the cassette.

DETAILED DESCRIPTION

Figure 1:
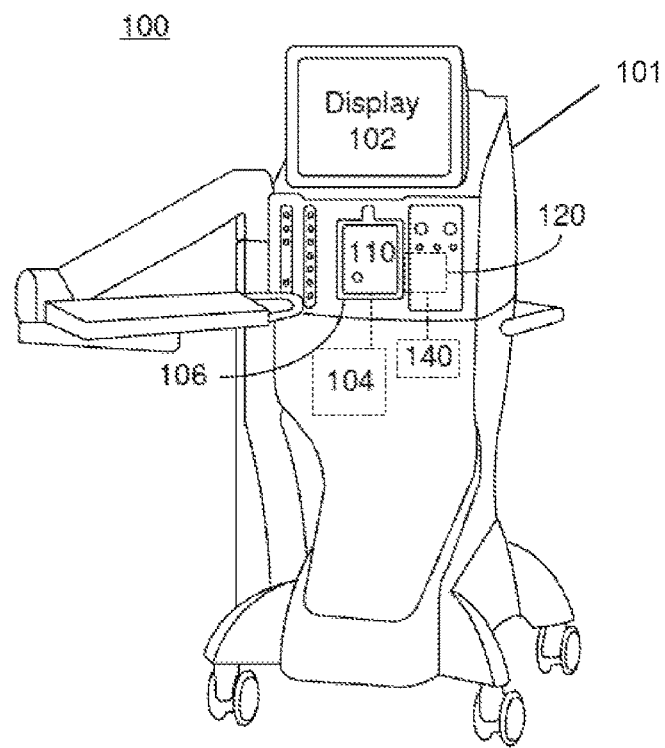
FIG. 1 is a diagram depicting an exemplary embodiment of a surgical system that measures internal cassette pressure using an interferometric pressure sensing system.

The exemplary embodiments relate to surgical systems, such as consoles used in ophthalmic surgery. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

The method and system are also described in terms of singular items rather than plural items. For example, a single cassette having a single interferometric pressure sensing system is used and/or shown in some embodiments. One of ordinary skill in the art will recognize that these singular terms encompass plural. For example, multiple cassettes and/or multiple interferometric sensing systems might be used.

In certain embodiments, the system includes one or more processors and a memory. The one or more processors may be configured to execute instructions stored in the memory to cause and control some or all of the process(es) set forth in the drawings and described below. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of an entirely hardware embodiment, an entirely software embodiment (including firmware, resident software, micro-code, etc.) or an embodiment combining software and hardware aspects. Furthermore, aspects of the method and system may take the form of a software component(s) executed on at least one processor and which may be embodied in one or more computer readable medium(s) having computer readable program code embodied thereon.

A method and system provide a surgical system including a cassette, a console and an interferometric pressure sensing system coupled with the console. The cassette is for exchanging material with a patient and includes a wall and a reflector. The wall undergoes a deflection in response to a nonambient internal cassette pressure. The console is coupled with the cassette. The interferometric pressure sensing system is coupled with the console. The interferometric pressure sensing system includes a light source and a detector. The light source provides a first portion of light that is reflected off of the reflector and a second portion of light that bypasses the reflector. The first portion and the second portion of light are recombined to form an interference pattern. The deflection corresponds to a shift in the interference pattern detectable by the detector.

Figure 2:
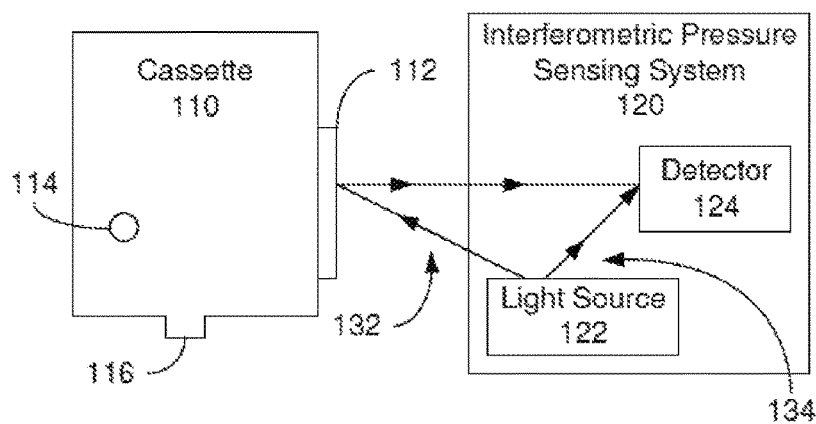
FIG. 2 depicts another exemplary embodiment of a portion surgical system that measures internal cassette pressure using an interferometric pressure sensing system.

FIG. 1 depicts a perspective view of an exemplary embodiment of a surgical system 100 usable in ophthalmic surgery. FIG. 2 depicts a portion of the surgical system 100. Referring to FIGS. 1-2, the surgical system 100 includes a console 101, a cassette 110 and an interferometric pressure sensing system 120. FIGS. 1-2 are not to scale and for explanatory purposes only. Thus, the system 100 is not limited to a particular console 101, cassette 110 or interferometric sensing system 120. For example, although a particular location of the cassette 110 in the console 101 and geometry are shown in FIG. 1, the surgical system 100 is not limited to the location and geometry depicted. For simplicity, not all portions of the console 101 are shown or labeled. The console 101 is coupled with the cassette 110 and the interferometric sensing system 120. During use, the console 101 is also typically connected with a surgical handpiece (not shown). The surgical handpiece may include an aspiration line and/or irrigation line connected to the console 101 via tubing (not shown) and electronics that are connected to and controlled by the console 101.

The console 101 includes a display 102, associated electronics (not explicitly depicted or labeled), a vacuum/pressure source 104, a receptacle 106 for receiving the cassette 110, and detection unit 140. In some embodiments, the console 101 may include both a vacuum source and a pressure source. In such embodiments, the sources are coupled to different cassettes that may reside in the same or different receptacles. However, for simplicity, the surgical system 100 is described in the context of a single receptacle 106, a single cassette 110 and a single vacuum/pressure source 104. The source 104 is primarily described in the context of a vacuum source 104. An analogous the discussion applies for a fluid/pressure source. Although depicted as part of the console 101 in FIG. 1, the detection unit 140 may be part of the interferometric pressure sensing system 120. Detection unit 140 is communicatively coupled to interferometric pressure sensing system 120 and other components of system 100. In certain embodiments, detection unit 140 may comprise one or more processors and memory configured to receive one or more signals from pressure sensing system 120 (e.g., signals indicating an interference pattern or shift in an interference pattern generated by detector 124) and determine cassette pressure based on the received signal(s) based on stored data correlating shifts or changes in interference patterns with internal cassette pressure and/or wall deflection, as described herein.

The vacuum/pressure source 104 is coupled to the cassette 110 through the receptacle 110. The vacuum/pressure source 104 may be a vacuum source such as a vacuum pump. In such an embodiment the vacuum source 104 provides a negative pressure (vacuum) to the cassette 110, which provides a vacuum to the aspiration line. In other embodiments, the vacuum/pressure source 104 may be a pressure source that provides a positive pressure to the cassette 110. The cassette 110 is coupled to a fluid source, which provides fluid to the irrigation line under the positive pressure. Alternatively, the vacuum/pressure source 104 may be a fluid source that can be placed under positive (greater than atmospheric) pressure.

The cassette 110 is for exchanging material with a patient. In the embodiment shown, the cassette 110 receives tissue, fluid and/or other biological material from the patient's eye. In other embodiments, the cassette 110 might be used to provide fluid such as a BSS to the patient's eye. The cassette includes walls and an internal chamber (not explicitly labeled in FIG. 1). The cassette 110 also includes a reflector 112 that is shown in FIG. 2 (but not in FIG. 1). The reflector 112 may be a mirror or any other suitable reflector. The reflector 112 may be attached to or integrated into the wall. In some embodiments, therefore, the wall itself may be reflective. In certain examples, the wall may be coated with or coupled to a reflective material. The cassette 110 is oriented such that the reflector 112 is facing the interferometric sensing system 120. In the embodiment shown, the normal to the surface of the reflector 112 is perpendicular to the interferometric sensing system 120. The reflector 112 may be at an oblique angle from some or all of the interferometric sensing system 120 in other embodiments.

Also shown are ports 114 and 116. The port 114 may be connected to tubing (not shown) and, therefore, to a surgical handpiece. The port 116 is connected to the vacuum source 104. Thus, a vacuum is provided to the cassette 110 through the port 116, while suction is provided to the aspiration line via port 114. Biological material from the patient's eye is received in the cassette 110 via port 114. This biological material remains in the cassette 110. Thus, the cassette 110 isolates the vacuum source 104 from the biological material.

The interferometric pressure sensing system 120 is coupled with the console 101. In certain examples, the interferometric pressure sensing system 120 may be considered to be incorporated into the console 101. Thus, the interferometric pressure sensing system 120 being coupled with the console 101 includes but is not limited to some or all of the components of the interferometric pressure sensing system being part of the console 101. In other embodiments, the some or all components of the interferometric pressure sensing system need not be incorporated into the console 101. In such embodiments, the light used may be transmitted to the appropriate location, for example via fiber optic cables. Also in such embodiments, control and data signals may be transmitted between the console 101 and the interferometric pressure sensing system 120 via wiring.

The interferometric pressure sensing system 120 includes a light source 122 and a detector 124. The detector 124 may be a linear or areal detector array. In certain embodiments, detector 124 may include any suitable light detector (e.g., CMOS, CCD, etc.). In some embodiments, the light source 122 may include a laser. Multiple light sources might be used, particularly if the light produced is in phase and of the same wavelength. However, in general, a single light source 122 is present. The interferometric pressure sensing system 120 splits the light into a first portion and a second portion. In general a beam splitter or analogous component is used to split light from the source 122 into multiple portions. In FIG. 2, these portions of light are shown as two separate beams 132 and 134 emanating from the light source 122. However, one of ordinary skill in the art will recognize that the portions of light actually correspond to multiple beams having some physical width and slightly different trajectories.

A first portion of light 132 travels from the light source 122 to the wall of the cassette 110, where it impinges on reflector 112. The first portion of light 132 reflects off of the reflector 112 and travels to the detector 124. The second portion of light 134 takes a different path to the detector 124. The path taken by the second portion of light 134 excludes or bypasses the reflector 112. The path length of light includes the physical distance traveled and any phase changes. In the embodiment shown, the paths taken by the portions of light 132 and 134 to the detector 124 in the absence of a pressure/vacuum being applied to the cassette 110 have different physical lengths. In addition, the first portion of light 132 undergoes a one hundred and eighty degree phase change because of the reflection off of the reflector 112. The portions of light 132 and 134 are recombined/reunited at and/or near the detector 124. Because the path lengths for the two portions of light 132 and 134 differ for various locations across the detector 124, an interference pattern (not shown in FIGS. 1-2) is generated when the beams are combined. The spacing of the bright and dark fringes in the interference pattern depends upon the wavelength of light used. Using the detector 124 the locations of the bright and dark fringes of the interference pattern can be determined.

The bright and dark fringes of the interference pattern may be at particular locations when the cassette 110 is not under a vacuum or excess pressure. Stated differently, the interference pattern may be known for the case where the interior of the cassette 110 is at ambient pressure. Ambient pressure is the pressure of the environment surrounding the console 101. When the vacuum source is activated, the interior of the cassette 110 is at a nonambient pressure (i.e. under vacuum in this scenario). Because the interior pressure of the cassette 110 is less than the ambient pressure, the wall(s) of the cassette may bend inward. Thus, the wall facing the interferometric pressure sensing system 120 may deflect. This deflection changes the position and, in some embodiments, shape of the reflector 112. This deflection also changes the physical path length for the first portion of light 132 by an amount proportional to the deflection. As a result, the pattern of fringes changes. For example, the fringes may shift location. This shift in location is based both on the wavelength of light used and the size of the deflection. In general, the shift is proportional to the deflection and inversely proportional to the wavelength of the light in the portions 132 and 134. Thus, shorter wavelength light yields a higher sensitivity in detection of the deflection.

Because the detector 124 can determine the locations of the fringes, the shift in the interference pattern may also be measured using the detector 124. Using the measured shift, the deflection in the wall of the cassette 110 may be determined. Based on known properties of the walls of the cassette and/or a previous calibration, the internal cassette pressure causing this deflection may be ascertained. The calibrations may be made prior to use in surgery using an internal pressure sensor (not shown) in the cassette 110. Alternatively, another method of calibration may be used. In certain embodiments, system-specific calibration data correlating fringe shift values with internal cassette pressure and/or cassette wall deflection values may be stored in memory (e.g., a memory of detection unit 140) and used by one or more processors (e.g., a processor of detection unit 140) to determine pressure values based on the interference pattern associated with the received light beam.

In some embodiments, the internal pressure of cassette 110 may be calculated by the detection unit 140 based on the shift in the interference pattern and calibration. For example, detector 124 may receive the recombined light beam and generate a signal indicating the location of bright and/or dark fringes of the interference pattern. Detection unit 140 may include hardware (e.g., one or more processor(s) and memory) and/or software configured to receive the signal from detector 124. In a calibration phase, the detector 124 may send a signal to a processor of detection unit 140 indicating the location of fringes when the cassette is in various pressurized states, including a non-pressurized state (e.g., before a surgical procedure begins). Detection unit 140 may store this calibration fringe location information in memory. During a procedure, the detector 124 may send signals to detection unit 140 indicating the location of fringes as the cassette is in use during the procedure. As explained above, the location of the fringes will shift due to deflection in the wall of the cassette 110, which alters the light beam reflected by reflector 112. Accordingly, the processor of detection unit 140 may analyze the received signals indicating fringe location to determine cassette pressure. For example, the processor may compare signals received at different times (e.g., during a procedure) to calculate or determine a fringe shift. Based on the fringe shift, the processor of detection unit 140 may determine internal cassette pressure and/or the deflection in the cassette wall using data stored in memory that correlates fringe shift values with internal cassette pressure and/or deflection values. In some embodiments, the detection unit 140 includes a digital signal processor (DSP) used in processing the signal from the interferometric pressure sensing system 120. In other embodiments, the internal pressure of the cassette 110 may be determined using a block (not shown) within the interferometric pressure sensing system 120. A processor of detection unit 140 may then output a signal indicating the determined internal cassette pressure so that other components of system 100 may respond as appropriate by, for example, increasing or decreasing pressure in the eye to maintain a target pressure.

Thus, using the interferometric pressure sensing system 120, the internal pressure of the cassette 110 may be determined. Because interferometry is used, the interferometric pressure sensing system 120 may more accurately determine pressure than, for example, the reflection method described above. The sensitivity of the interferometric pressure sensing system may be set using the wavelength of light from the light source. A lower wavelength light source 122 may be used to obtain a higher sensitivity measurement. Thus, the interferometric pressure sensing system 120 may be relatively easily tuned at the design phase. Because the interferometric pressure sensing system 120 is external to the cassette 110, the pressure measurement is non-invasive. There is essentially no risk of the biological material removed from the patient contacting the interferometric pressure sensing system 120. Thus, the interferometric pressure sensing system 120 may be less expensive and less likely to fail. Although the reflector 112 is added to the cassette 110, the reflector 112 is relatively inexpensive. Not only may the internal pressure of the cassette 110 be more accurately measured, but the cost may also be reduced. Further, the interferometer used in the interferometric pressure sensing system 120 may be small. As a result, the interferometric pressure sensing system 120 may be relatively compact.

Figure 3A:
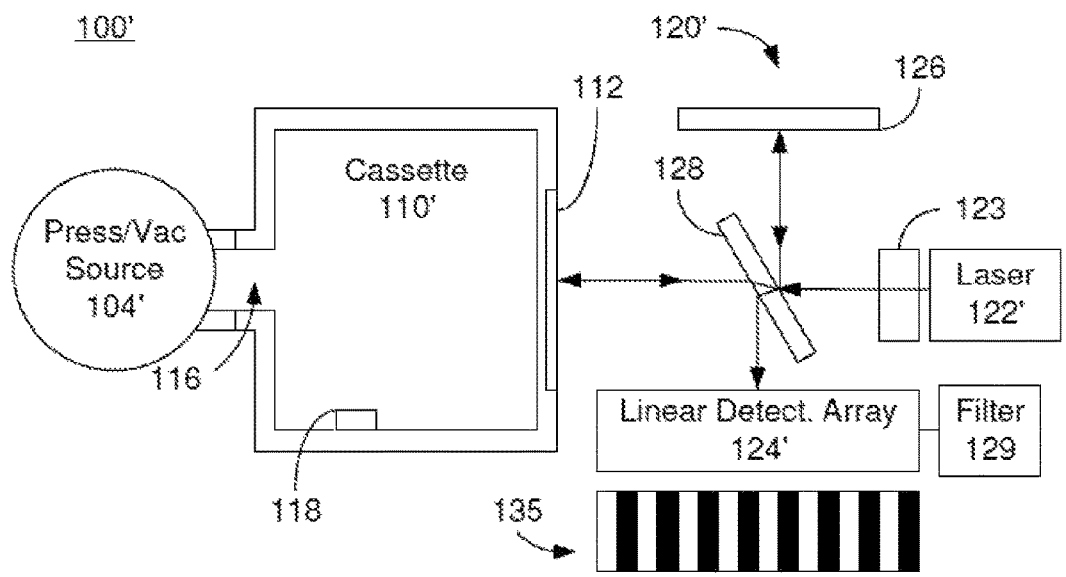
FIGS. 3A-3C depict another exemplary embodiment of a surgical system that measures internal cassette pressure using an interferometric pressure sensing system.
Figure 3B:
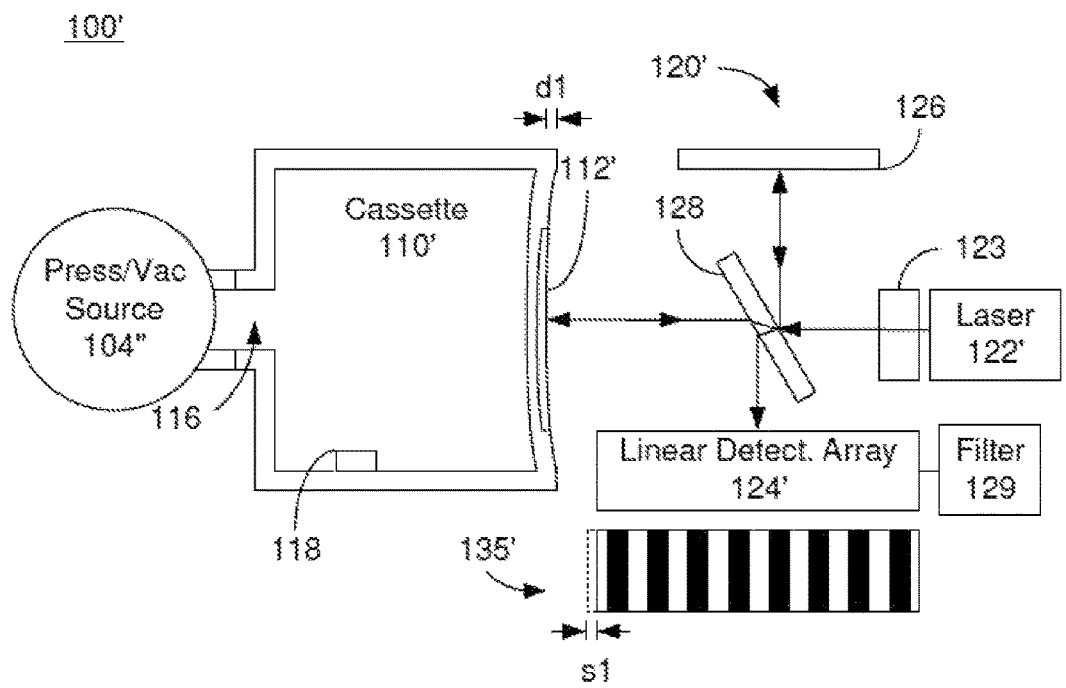
Figure 3C:
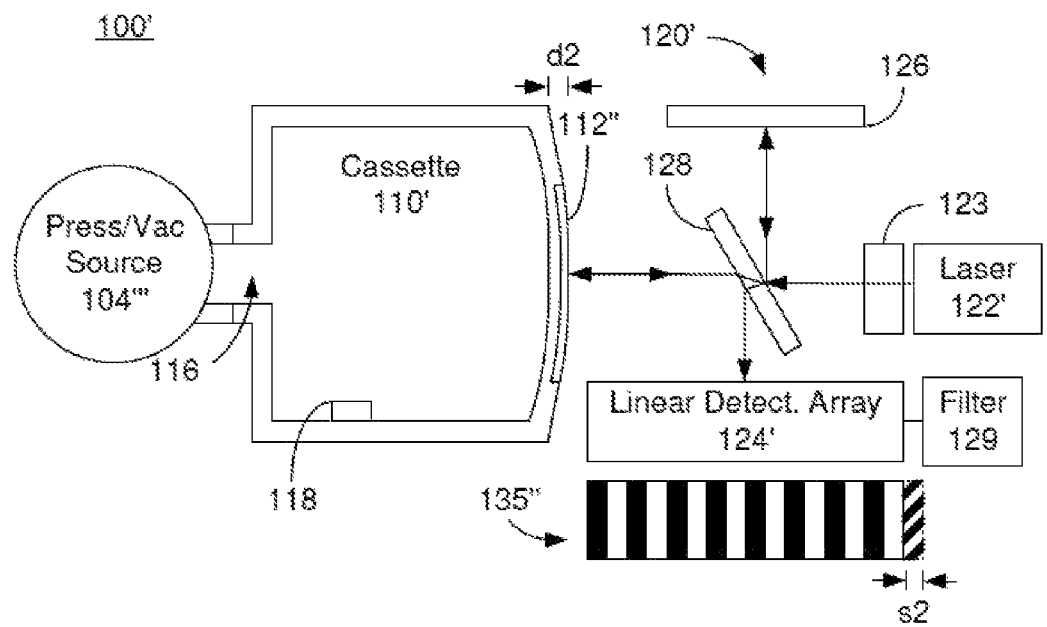

FIGS. 3A-3C depict another exemplary embodiment of a surgical system 100' that measures pressure using an interferometric pressure sensing system. FIGS. 3A-3C are not to scale and for explanatory purposes only. Thus, a particular surgical system is not intended to be shown. FIG. 3A depicts the surgical system 100' when the cassette 110' is at ambient (zero applied) pressure. FIG. 3B depicts the surgical system 100' when the cassette is under vacuum (less than ambient internal pressure). FIG. 3C depicts the surgical system 100' when the cassette 110' is under pressure (greater than ambient internal pressure). In general, a cassette is either placed under pressure or under vacuum, not both. However, both conditions are shown for the same cassette in order to explain operation of the surgical system 100'.

The surgical system 100' is analogous to the surgical system 100. Analogous components have similar labels. The surgical system 100' includes a console (not explicitly labeled), a cassette 110' and an interferometric pressure sensing system 120' analogous to components 101, 110 and 120, respectively. The pressure/vacuum source 104' of the console is shown. The cassette 110' may reside in the receptacle of the console. The port 114 of the cassette and analogous features are not shown.

The cassette 110' is used to isolate the pressure/vacuum source 104' from the biological material. The cassette 110' includes the port 116 coupled with the pressure/vacuum source 104' and the reflector 112. In this embodiment, the reflector 112 is integrated into the wall of the cassette 110'. In addition, the cassette 110' includes an optional internal pressure sensor 118. The internal pressure sensor 118 is used in calibrating the cassette 110'. Consequently, the internal pressure sensor 118 may not be used during surgery.

The interferometric pressure sensing system 120' is coupled with the console and takes the form of a Michelson interferometer. In other embodiments another interferometer might be used. The interferometric pressure sensing system 120' includes a laser light source 122', a detector 124', an optional optical isolator 123, additional reflector 126, beam splitter 128 and optional filter 129. The optical isolator 123 may be used to prevent reflected light from reaching the laser 122'. The beam splitter 128 divides the light from the laser 122' into two portions. The beam splitter 128 is also used in recombining the light in the embodiment shown. The beam splitter 128 may be a partially silvered mirror. The detector 124' is a linear detector array. The filter 129 may be used to filter the signal from the detector 124'. The filter 129 may be a low pass filter. For example, the filter 129 may pass signals having a frequency less than one hundred Hertz. In some such embodiments, the filter 129 may pass signals having a frequency of less than sixty Hz. Other threshold frequencies may be used to define the pass band for the filter 129. For example, a band pass or other mechanism for reducing noise may be used. In other embodiments, another component such as a DSP might be used to process the signal from the detector 124' in place of the filter 129.

Light from the laser 124' passes through the isolator 123 and strikes the beam splitter 128. A first portion of the light is transmitted and refracted by the beam splitter 128 and reaches the reflector 112. The reflector 112 reflects the first portion of the light back to the beam splitter 128. Because the beam splitter 128 is a partially silvered mirror, this portion of light is also reflected down to the linear detector array 124. A second portion of the light is reflected by the beam splitter 128 to the additional reflector 126. This second portion of light is reflected back from the reflector 126 to the beam splitter 128. The second portion of light is also transmitted by the beam splitter 128 to the linear detector array 124'. The two portions of light are recombined, resulting in an interference pattern 135 at the linear detector array 124'.

In this example, the two portions of light have traveled different physical paths. Both portions of light have undergone two reflections, each of which would alter the phase by one hundred and eighty degrees. The first portion is first reflected off of the reflector 112 and then off of the beam splitter 128. The second portion is first reflected off of the beam splitter 128 and then off of the reflector 126. The phase difference between the two portions that are recombined at the linear detector array 124 is due to the difference in physical path lengths. In other embodiments, any phase difference may be due partly to a difference in physical path lengths and partly to phase inversion(s) at reflection(s). As can be seen in FIG. 3A, the interference pattern 135 is formed for the cassette 110' at the ambient internal pressure.

FIG. 3B depicts the system 100' when the vacuum source 104" provides a vacuum. Such a vacuum is typically measured in millimeters of mercury. For example, a vacuum of six hundred or seven hundred millimeters of mercury might be applied. In such cases, the internal pressure of the cassette 110' is six hundred or seven hundred millimeters of mercury less than the ambient pressure. Because the internal pressure of the cassette 110' is less than the ambient pressure, the wall of the cassette 110' undergoes a deflection analogous to that shown in FIG. 3B. The reflector 112' also undergoes a deflection. This deflection increases the distance between the beam splitter 128 and the reflector 112' by the deflection, d1. The resulting increase in the distance traveled by the first portion of light being reflected by the reflector 112' is approximately twice the deflection. Thus, the physical path length is increased by approximately twice the deflection for this portion of light. However, the path length has not been changed for the second portion of light reflecting off of the reflector 126. As a result, the interference pattern 135' shifts by a distance s1. If the vacuum source 104" applies the vacuum during calibration, then the internal pressure sensor 118 may be used to measure the internal pressure and calibrate the shift s1 to the deflection d1 and to the internal pressure. Such data may be stored in memory of detection unit 140, as noted above. If the vacuum source 104" provides the vacuum in order to apply suction to a patient's eye via an aspiration line (not shown), the sensor 118 is not used. Instead, the calibration previously obtained and the measured shift s1 and deflection d1 are used to ascertain the internal pressure of the cassette 110'.

FIG. 3C depicts the system 100' when the vacuum/pressure source 104''' provides a positive pressure to the cassette 110'. For example, a pressure of eighty psi or more might be applied in some embodiments. Because the internal pressure of the cassette 110' is greater than the ambient pressure, the wall of the cassette 110' undergoes a deflection analogous to that shown in FIG. 3C. The reflector 112" also undergoes a deflection. This deflection decreases the distance between the beam splitter 128 and the reflector 112" by the deflection, d2. The resulting decrease in the distance traveled by the first portion of light being reflected by the reflector 112" is approximately twice the deflection. However, the path length has not been changed for the second portion of light reflecting off of the reflector 126. As a result, the interference pattern 135" shifts by a distance s2. In the embodiment shown, the shift s2 is in a different direction and has a different magnitude than the shift s1. Other shifts are possible. If the vacuum/pressure source 104''' applies the pressure during calibration, then the internal pressure sensor 118 may be used to measure the internal pressure and calibrate the shift s2 to the deflection d2 and to the internal pressure. Such data may be stored in memory of detection unit 140, as noted above. If the vacuum source 104''' provides the pressure in order to supply fluid to a patient's eye via an irrigation line (not shown), the sensor 118 is not used. Instead, the calibration previously obtained, shift s2 and deflection d2 are used to measure the internal pressure of the cassette 110'.

The system 100' shares the benefits of the system 100. Using the interferometric pressure sensing system 120', the internal pressure of the cassette 110' may be determined (e.g., by a processor and memory of detection unit 140 communicatively coupled to system 120'). The interferometric pressure sensing system 120' may be more accurate because interferometry is used. The interferometric pressure sensing system 120' is external to the cassette 110'. Thus, there is little to no risk of the biological material removed from the patient contacting the interferometric pressure sensing system 120'. The addition to the disposable cassette 110', the reflector 112/112'/112", is relatively inexpensive. Thus, not only may the internal pressure of the cassette 110 be more accurately measured, but the cost may also be reduced. Further, because the interferometer used in the interferometric pressure sensing system 120' may be small, the interferometric pressure sensing system 120 may be relatively compact.

Figure 4:
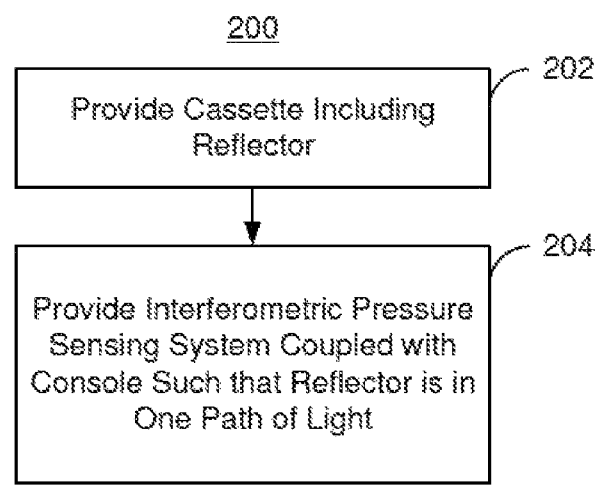
FIG. 4 is a flow chart depicting an exemplary embodiment of a method for providing a surgical system.

FIG. 4 is an exemplary embodiment of a method 200 for providing a surgical system such as the surgical system(s) 100 and/or 100'. For simplicity, some steps may be omitted, interleaved, and/or combined. The method 200 is also described in the context of the surgical system 100. However, the method 200 may be used to form the surgical system 100' and/or an analogous surgical system.

The cassette 110 including a reflector 112 is provided, via step 202. Step 202 may include forming the cassette 110 and attaching the reflector 112. Alternatively, the reflector 112 might be integrated into the wall of the cassette. In other embodiments, some or all of the wall of the cassette may be formed by the reflector 112. In certain examples, some or all of the wall of the cassette may be coated with a reflective material.

The interferometric pressure sensing system 120 is provided and coupled with the console 101, via step 204. Step 204 may include forming the interferometric pressure sensing system 120 as part of the console 101. In other embodiments, a separate interferometric sensing system 120 may be provided and connected to the console 101 via fiber optic cables, wiring, or other means. Components of the disclosed systems such as light source 122, reflector 112, beam splitter 128, reflector 126, and detector 124 are optically aligned. Using the method 200, the surgical system 100 and/or 100' may be fabricated. Thus, the benefits of one or more of the surgical systems 100 and/or 100' may be achieved.

Figure 5:
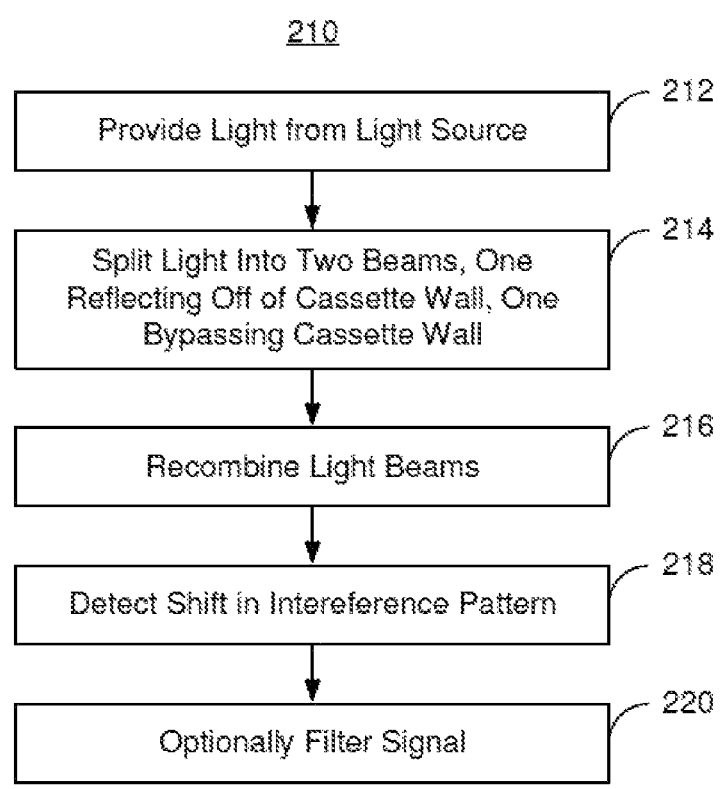
FIG. 5 is a flow chart depicting an exemplary embodiment of a method for assisting a physician using the surgical system.

FIG. 5 is a flow chart depicting an exemplary embodiment of a method 210 for measuring an internal cassette pressure using a deflection in the wall of the cassette during ophthalmic surgery. For simplicity, some steps may be omitted, interleaved, performed in another order and/or combined. The method 210 may include executing instructions on one or more processors of system 100 configured to execute software instructions stored in memory. Further, the method 210 is described in the context of ophthalmic surgery using the surgical system 100. However, the method 210 may be extended to other types of surgery.

The method commences after surgery has started. Thus, the surgeon has made incision(s) in the eye of the patient, performed other required tasks, and inserted the aspiration and/or irrigation line(s) in the eye of the patient. The interferometric pressure sensing system 120 has also been calibrated, for example using an internal sensor. The pressure in the cassette 110 may be greater than ambient if the cassette 110 is used to provide fluid to the patient's eye. The pressure in the cassette 110 may be less than ambient if the cassette 110 is used to extract material from the eye.

Light is provided from the light source 122, at step 212. Step 212 may include activating the laser 122. The laser 122 may be controlled to be powered on and off intermittently power or may be simply powered on during use. Step 212 may also include allowing the light to pass through an isolator, such as the optical isolator 123.

The light from the light source is split into two portions, at step 214. Step 214 may be carried out by passing the light through a beam splitter such as the splitter 128. Because of the configuration of the interferometric pressure sensing system 120, the first portion of light is reflected off of the reflector 112, while the second portion of light bypasses the reflector 112. In some embodiments, the second portion of light is reflected off of the second reflector 126.

The light that has traversed different paths is recombined, at step 216. Step 216 may simply include allowing the light to pass back through the beam splitter 128 in a manner analogous to that shown in FIGS. 3A-3C. Thus, an interference pattern is developed. There may be a shift in the interference pattern if the pressure within the cassette 110 differs from the ambient.

If present, a shift in the interference pattern is detected, at step 218. Step 218 may include detecting the interference pattern using light detector 124 and a processor of detector unit 140. In certain examples, signals indicating a detected interference pattern, fringe position, or shift in fringe position may be transmitted to and received by a processor. The processor may be configured to analyze the signals to determine whether any shift is present and, if so, the size and magnitude of the shift. The processor may further use determined shift data to determine an internal cassette pressure and/or wall deflection, and to output a signal to other components of system 100 indicating the determined pressure. Thus, step 218 may include not only obtaining a signal from the detector 124, but also processing the signal, determining shift, pressure, and deflection, and generating an output signal indicating pressure and/or deflection. One or more aspects of step 218 may be performed using software executed by a processor of detection unit 140. The signal may also be filtered, at step 220. Step 220 may be performed using a low pass filter. Alternatively, a band pass filter may be used to synchronize detection of the shift with the intermittent laser pulses if the light source 122 is powered on and off in step 212. In some embodiments, step 220 occurs before or is part of step 218. Thus, detection of the shift may be isolated from vibrations due to the pump or other sources of noise.

Using the method 210 and pressure within the cassette 110/110' may be noninvasively detected during use in surgery. Consequently, various benefits of the surgical systems 100 and/or 100' may be achieved. A method and system for providing a surgical system that can interferometrically determine cassette pressure during ophthalmic surgery, have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

What is claimed is:

1. A surgical system comprising:
a cassette for exchanging material with a patient, the cassette including a wall and a reflector, the wall configured to undergo a deflection in response to a nonambient internal cassette pressure;
a console coupled with the cassette; and
an interferometric pressure sensing system coupled with the console, the interferometric pressure sensing system including a light source and a detector, the light source providing a first portion of light that is reflected off of the reflector and a second portion of light bypassing the reflector, the first portion and the second portion recombining to form an interference pattern, the deflection corresponding to a shift in the interference pattern detectable by the detector.

2. The surgical system of claim 1 wherein the interference pattern results from a difference in the physical paths of the first portion of the light and the second portion of the light.

3. The surgical system of claim 2 wherein the interferometric pressure sensing system includes a Michelson interferometer.

4. The surgical system of claim 3 wherein the Michelson interferometer includes a beam splitter and an additional reflector, the light from the light source passing through the beam splitter to form the first and second portions of the light, the additional reflector being coupled with a portion of the console.

5. The surgical system of claim 1, further comprising a processor configured to:
receive a signal from the detector related to the interference pattern;
based on the received signal, calculate the shift in the interference pattern; and
based on the calculated shift, determine a cassette pressure.

6. The surgical system of claim 1 wherein the light source and detector are integrated into the console.

7. The surgical system of claim 1 wherein the reflector is integrated into the wall of the cassette.

8. The surgical system of claim 1 wherein the reflector is coupled with the wall of the cassette.

9. The surgical system of claim 1 wherein the light source is a laser.

10. The surgical system of claim 1 wherein the light source has a wavelength and wherein the shift in the interference pattern corresponds to twice the deflection divided by the wavelength.

11. The surgical system of claim 1 wherein the nonambient pressure is greater than ambient pressure and the deflection is such that the reflector is closer to the detector.

12. The surgical system of claim 1 wherein the nonambient pressure is less than ambient pressure and the deflection is such that the reflector is further from the detector.

13. The surgical system of claim 1 wherein the interferometric pressure sensing system further includes a low pass filter coupled with the detector, the low pass filter for transmitting a signal that corresponds to the shift, the low pass filter having a pass band less than a threshold frequency.

14. The surgical system of claim 1 wherein the console includes a receptacle configured to receive the cassette.

15. An interferometric pressure sensing system for a surgical cassette, comprising:
a light source, configured to provide a light beam;
a beam splitter, configured to:
direct a first portion of the light beam towards a reflector on a wall of the surgical cassette, the wall configured to deflect in response to a nonambient internal cassette pressure; and
direct a second portion of the light beam to bypass the reflector en route to a detection unit;
the detection unit comprising a light beam sensor, a processor, and a memory, configured to:
receive a recombined light beam comprising the first portion reflected by the reflector and the second portion of the light beam which bypassed the reflector;
detect an interference pattern associated with the recombined light beam;
analyze the detected interference pattern to identify a shift in the interference pattern, the shift corresponding to a deflection of the wall of the surgical cassette; and
determine an internal cassette pressure based on the identified shift.

16. A method for treating an ophthalmic condition in an eye of a patient using a surgical system including a cassette and a console coupled with the cassette, the cassette including a wall, the method comprising:
providing light from a light source;
splitting the light into a first portion and a second portion, wherein:
the first portion is reflected off of a reflector on the wall of the cassette such that a first path of the first portion of the light includes the reflector, and the second portion bypasses the reflector such that a second path of the second portion excludes the reflector;

recombining the first portion and the second portion to form an interference pattern, and detecting a shift in the interference pattern, the shift in the interference pattern corresponding to a deflection in the wall of the cassette caused by a nonambient internal cassette pressure.

17. The method of claim 16, further comprising determining the deflection in the wall of the cassette based on the detected shift in the interference pattern.

18. The method of claim 16, further comprising determining the internal cassette pressure based on the detected shift in the interference pattern.

19. The method of claim 16, further comprising low-pass filtering a signal corresponding to the shift to provide a filtered signal having a frequency less than a threshold frequency.

* * * * *